(12) United States Patent
Carr et al.

(10) Patent No.: US 8,399,701 B2
(45) Date of Patent: Mar. 19, 2013

(54) PROCESS FOR THE PREPARATION OF DI- AND POLYAMINES OF THE DIPHENYLMETHANE SERIES

(75) Inventors: Robert Henry Carr, Bertem (BE); Peter Muller, SM Hellevoetsluis (NL); Rabah Mouazer, Wavre (BE)

(73) Assignee: Huntsman International LLC, The Woodlands, TX (US)

( * ) Notice: Subject to any disclaimer, the term of this patent is extended or adjusted under 35 U.S.C. 154(b) by 421 days.

(21) Appl. No.: 12/601,577

(22) PCT Filed: May 16, 2008

(86) PCT No.: PCT/EP2008/056019
§ 371 (c)(1),
(2), (4) Date: Nov. 24, 2009

(87) PCT Pub. No.: WO2008/148631
PCT Pub. Date: Dec. 11, 2008

(65) Prior Publication Data
US 2010/0174114 A1  Jul. 8, 2010

(30) Foreign Application Priority Data
Jun. 4, 2007 (EP) .................................. 07109480

(51) Int. Cl.
*C07C 211/00* (2006.01)
*C07C 265/00* (2006.01)
*C07C 263/00* (2006.01)

(52) U.S. Cl. .................... 560/330; 560/347; 564/326

(58) Field of Classification Search .................. None
See application file for complete search history.

(56) References Cited

U.S. PATENT DOCUMENTS

| 5,756,063 A | 5/1998 | Nuernberg et al. |
| 7,186,857 B2 * | 3/2007 | Muller et al. ............ 560/330 |
| 2003/0045745 A1 | 3/2003 | Hagen et al. |
| 2006/0094897 A1 | 5/2006 | Muller et al. |

FOREIGN PATENT DOCUMENTS

| EP | 1288190 A | 3/2003 |
| EP | 1652835 A | 5/2006 |

OTHER PUBLICATIONS

H. J. Twitchett, "Chemistry of the Production of Organic Isocyanates" Chem. Soc. Rev. 3(2), p. 209-230 (1974).
William M. Moore, "Amines, Aromatic (Methylenedianiline)", Kirk-Othmer Encyclopedia of Chemical Technology, $3^{rd}$ Ed., New York, 2, p. 338-348 (1978).

* cited by examiner

*Primary Examiner* — Karl J Puttlitz
(74) *Attorney, Agent, or Firm* — Robert A. Diaz

(57) ABSTRACT

The present invention relates to a process for the preparation of di- and polyamines of the diphenylmethane series, and to the preparation of di- and polyisocyanates of the diphenylmethane series from these di- and polyamines. The di- and polyamines of the diphenylmethane series are prepared by the reaction of aniline and formaldehyde in the presence of hydrochloric acid. In the present invention, the formaldehyde employed is used as an aqueous solution which contains less than 0.001 wt % of metal ions which are divalent and/or more than divalent.

11 Claims, No Drawings

PROCESS FOR THE PREPARATION OF DI- AND POLYAMINES OF THE DIPHENYLMETHANE SERIES

CROSS REFERENCE TO RELATED APPLICATIONS

This application is the National Phase of International Application PCT/EP08/056019 filed May 16, 2008 which designated the U.S. and which claims priority to EP Patent App. No. 07109480.9 filed Jun. 4, 2007. The noted applications are incorporated herein by reference.

The present invention relates to a process for the preparation of di- and polyamines of the diphenylmethane series.

Di- and polyamines of the diphenylmethane series are understood as meaning compounds and compound mixtures of the following structure:

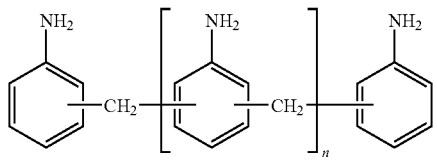

wherein n represents a natural number equal to or greater than zero.

The continuous, discontinuous, or semi-continuous preparation of di- and polyamines of the diphenylmethane series, also called MDA in the following text, is described in numerous patents and publications. See e.g. H. J. Twitchett, Chem. Soc. Rev. 3(2), 209 (1974), M. V. Moore in Kirk-Othmer Encycl. Chem. Technol., 3rd ed., New York, 2, 338-348 (1978). The preparation of these polyamines is conventionally carried out by reaction of aniline and formaldehyde in the presence of acidic catalysts. Aqueous hydrochloric acid is conventionally employed as the acidic catalyst. According to the prior art, the acidic catalyst is neutralized by addition of a base, and thus, used up at the end of the process, and before the final working-up steps (such as, for example, removal of excess aniline by distillation). Conventionally, formaldehyde is employed industrially as an aqueous solution which is present in concentrations of 30 to 50 wt %. However, it is also possible to employ aqueous formaldehyde solutions of another concentration, or other compounds which supply methylene groups. Other such suitable compounds include, for example, polyoxymethylene glycol, para-formaldehyde; methylal or trioxane.

The di- and polyisocyanates of the diphenylmethane series, called MDI in the following text, are prepared by phosgenation of the corresponding di- and polyamines (MDA). The di- and polyisocyanates of the diphenylmethane series which are prepared in this way thereby contain the various isocyanate isomers and higher homologues thereof in the same composition as the polyamines from which they have been prepared. Any of the many and varied phosgenation and associated work-up processes are applicable for conversion to MDI of the MDA prepared according to the current process.

It is critical for the subsequent use of the polyisocyanates in the manufacture of polyurethanes or other materials or products that levels of impurities are generally at low and relatively consistent concentrations. Especially noteworthy in this regard are levels of chlorinated impurities [yielding so-called "ionisable" and "hydrolysable" chlorine and the like] which can interfere with the amine catalysts typically used in polyurethane manufacture.

In the course of the preparation of MDA, the acidic reaction mixture is conventionally neutralized with a base. After the neutralization, the organic phase is conventionally separated from the aqueous phase in a separating container. The product-containing organic phase which remains after the aqueous phase has been separated off is then conventionally subjected to further working-up steps, such as a washing with water, and then freed from excess aniline and other substances present in the mixture (e.g. further solvents) by, for example, distillation, extraction or crystallization.

Experience in the plant shows, however, that separating off of the aqueous phase from the product-containing organic phase after the neutralization and/or the subsequent washing, may be severely impaired by the formation of a third phase (rag or rag layer). This third phase is a stable, possibly voluminous intermediate phase typically characterised by the presence of solids, which occurs between the aqueous and the organic phases, and makes phase separation difficult. In the extreme case, this third phase even prevents phase separation completely. In the most adverse case for the process in the plant, the phase separation tank or tanks affected must be emptied completely and cleaned. The content of the phase separation tank or tanks then has to be worked-up or disposed of with great effort, which is associated with considerable costs. Under certain circumstances this can also lead to the continuous production having to be interrupted.

The presence of a relatively small amount of solids at the neutralisation stage can be tolerated from the perspective of plant operation if the quantity is sufficiently low that the required separations can be carried out. In a continuous process, the rate of build up of the solids to form a rag layer may also be sufficiently low as to allow production to continue for some time before having to interrupt the process.

However, it has surprisingly been found that the presence of these solids in the MDA at levels which do not cause problems in MDA production can lead to problems in MDI production and, ultimately, in the eventual use of the isocyanate products. For example, in the production process converting MDA to MDI, solids present in the original MDA can contribute to fouling of a range of process equipment including but not limited to climbing film evaporators, falling film evaporators, nozzles, distillation column trays and packings, in-line filters and the like or can catalyse undesirable side reactions such as formation of dichlorobenzenes from the monochlorobenzene phosgenation solvent. Still further problems arising from the presence of these solids in the MDA being used to make MDI can include but are not limited to the final MDI products being hazy in appearance or having varying and unexpected reactivity when reacted with a range of polyether or polyester polyols in the manufacture of desired polyurethane products.

It is thus an object of the present invention to provide a simple and economical process for the preparation of di- and polyisocyanates of the diphenylmethane series which is free of certain operational problems and which yields isocyanate products with desired properties such as reactivity.

It is a further object of the present invention to provide a simple and economical process for the preparation of di- and polyamines of the diphenylmethane series in which the separating off of the aqueous phase from the product-containing organic phase, after the neutralization and/or the subsequent washing, can be carried out simply and without trouble.

The invention relates to a process for the preparation of di- and polyamines of the diphenylmethane series comprising reacting aniline with formaldehyde in the presence of hydrochloric acid, whereby the formaldehyde employed is used as an aqueous solution which contains less than 0.001 wt % of metal ions which are divalent and/or more than divalent.

Another aspect of the present invention is a process for the preparation of di- and polyisocyanates of the diphenylmethane series from these di- and polyamines of the diphenylmethane series. This process comprises reacting the di- and polyamines of the diphenylmethane series that are produced by the previously described process with phosgene, to yield the corresponding di- and polyisocyanates of the diphenylmethane series.

Another aspect of the present invention is provision of on-line analysis methodology in order to monitor the purity of the used aqueous formaldehyde solution such that process control can be undertaken prior to problematic rag layer formation in the event of decreased formaldehyde solution purity.

In accordance with the present invention, the limit of less than 0.001 wt % relates to the sum of the concentrations of the metal ions which are divalent and/or metal ions which are more than divalent. Preferably, the aqueous formaldehyde solution employed in the present invention contains less than 0.0005 wt % (i.e. 0 to <0.0005 wt %), and most preferably less than 0.0003 wt % (i.e. 0 to <0.0003 wt %) of metal ions which are divalent and/or metal ions which are more than divalent.

The formaldehyde required for the preparation of MDA can originate from various sources or processes. Preferably, the aqueous formaldehyde solution is prepared by absorption of gaseous formaldehyde into water with sufficient purity, for example, demineralised water. In this context, the aqueous formaldehyde solution conventionally has a concentration of formaldehyde of 40 to 50 wt %, but higher or lower concentrations are also possible. Minor levels of impurities (for example methanol) and additives (for example, polyvinylalcohol as stabiliser) may be present.

As used in the present application, the phrase metal ions which are divalent and/or more than divalent is understood as meaning ions in an oxidation level greater than or equal to +2 of the metals originating from main groups 2 to 6, subgroups 1 to 8, the lanthanide series and/or the actinide series of the periodic table of the elements. Examples of such metals include, for example, alkaline earth metals, such as magnesium and calcium, or also metals such as aluminium and iron. The concentrations of the individual metal ions in the aqueous formaldehyde solution here are preferably less than 0.0003 wt. %.

Especially the presence of high amounts of iron has an influence on the final properties of the polyisocyanates in terms of uncontrolled reactivity with polyols in the preparation of polyurethane materials.

The process according to the invention can be carried out both continuously, and semi-continuously, and also discontinuously/batchwise.

Polyamines of the diphenylmethane series can be prepared with degrees of protonation of less than 15% by the process of the present invention, but higher degrees of protonation are also possible. In this context, in the case, of use of hydrochloric acid, the molar ratio of the amount of hydrochloric acid employed and the molar amount of amine functions present in the reaction mixture is called the degree of protonation.

Suitable polyamine mixtures of the diphenylmethane series are conventionally obtained by condensing aniline with formaldehyde in the molar ratio of 1.5:1 to 20:1.

According to a preferred embodiment high purity hydrochloric acid is used in the present process, said hydrochloric acid containing less than 0.001 wt % of metal ions which are divalent and/or metal ions which are more than divalent.

The concentration of the hydrochloric acid used in the process of the present invention is generally between 30 and 37 wt %.

In one embodiment of the process of the invention, the process comprises first mixing aniline with hydrochloric acid, and then adding aqueous formaldehyde solution to the mixture. Likewise, however, it is also possible to mix aniline, aqueous formaldehyde solution and hydrochloric acid in another sequence, or also to mix these simultaneously.

In accordance with the present invention, the process can be carried out, e.g., by a procedure comprising introducing aniline, aqueous formaldehyde solution and hydrochloric acid into a stirred tank, and mixing, and optionally, in parallel with the reaction which occurs, removing or separating some of the water by distillation. In a discontinuous process, aniline, formaldehyde solution and hydrochloric acid can optionally be added over time-based metering profiles, with it being possible to separate off the water during or after the addition of the educts by, for example, means of vacuum distillation. Preferably, the mixing of aniline, formaldehyde solution and aqueous HCl takes place at temperatures of 20 to 60° C.

In another embodiment, the invention comprises first mixing aniline and aqueous formaldehyde solution and reacting in the absence of the acidic catalyst at temperatures of 20° C. to 100° C., preferably 40° C. to 100° C., and most preferably 60° C. to 95° C. Condensation products of aniline and formaldehyde (i.e. so-called aminal) form during this procedure. After the aminal formation, the water contained in the aminal is at least partly removed by, for example, phase separation or by other suitable processes such as, for example, by distillation. Then, the aminal is mixed with hydrochloric acid, preferably at temperatures of 20 to 60° C. and preferably with specific power inputs of greater than 10 kW/m$^3$.

The addition of the acidic catalyst and the removal of the water can be carried out by, for example, a procedure in which aqueous HCl is introduced into a stirred tank containing the aminal produced, and optionally some of the water is removed by distillation during the reaction to give the condensation product.

The further reaction of the reaction mixture which is obtained according to one of the above embodiments is carried out in conventional reaction equipment. For example, suitable equipment includes stirred reactors, tube reactors and/or tube reactors with baffles such as perforated trays, which influence the residence time characteristics in the reactor. A combination of several types of reactor is also suitable.

Preferably, the temperature of the reaction mixture is brought in stages, or continuously, and optionally, under increased pressure to a temperature of 110° C. to 250° C., more preferably of 110° C. to 180° C., and most preferably of 110° C. to 160° C. The residence time required is chosen such that complete conversion is ensured.

The reaction of aniline and formaldehyde in the presence of hydrochloric acid can also be carried out in the presence of further substances. Other suitable substances include, for example, salts, organic acids, or inorganic acids.

In all cases, on-line monitoring of metal ions which are divalent and/or more than divalent in the aqueous formaldehyde solution is preferably carried out on the aqueous formaldehyde solution prior to its addition to any other reactants or reaction mixture. Suitable methods for analysis include those based on the characteristic electronic transitions which occur within the metal ions in various ranges of the electromagnetic spectrum. Thus, methods such as atomic absorption or emission spectroscopies (AAS or AES) or methods based on X-ray emission of absorption are preferred. Mass spectrometric techniques such as using an inductively-coupled plasma (ICP-MS) may also be used. For on-line analysis, the chosen technique can be used by means of a suitable sampling and sample preparation system, many of which have been described in the prior art. Alternatively, conventional sampling and laboratory-based analysis can be used. On-line analysis is preferred because of the more rapid provision of analytical data and, thus, enhanced opportunity for process control (either manually or via automated control systems).

In order to work up the acidic reaction mixture, the reaction mixture is conventionally neutralized with a base. According to the prior art, the neutralization is conventionally carried out at temperatures of, for example, 90 to 100° C., without the addition of further substances. (See H. J. Twitchett, Chem. Soc. Rev. 3(2), 223 (1974)). However, neutralization can also be carried out at another temperature level, in order to accelerate the breakdown of troublesome by-products. Suitable bases include, for example, the hydroxides of the alkali and alkaline earth metals. Aqueous NaOH is preferably used.

It is preferred that the base employed for the neutralization is employed in amounts of greater than 100%, and more preferably in 105% to 120% of the amount required stoichiometrically for the neutralization of the acidic catalyst employed. Minimisation of the excess is clearly beneficial on economic grounds.

After the neutralization, the organic phase is conventionally separated from the aqueous phase in a separating tank. The product-containing organic phase which remains after the aqueous phase has been separated off, is then conventionally subjected to additional working up steps (e.g. washing with water), and is then freed from excess aniline and other substances present in the mixture (e.g. further solvents) by suitable processes such as, for example, distillation, extraction or crystallization.

In accordance with the present invention, by the use of aqueous formaldehyde solution which contains less than 0.001 wt % of metal ions which are divalent and/or more than divalent, the separating off of the aqueous phase from the MDA-containing organic phase after the neutralization and/or the subsequent washing, can be carried out simply and without trouble. This is due to the low contents of metal ions which are divalent and/or more than divalent in the aqueous formaldehyde solution which have the effect that a third phase (i.e. rag or a rag layer) which interferes with the phase separation or makes phase separation difficult, is no longer formed.

The di- and polyamines prepared in this way can be reacted with phosgene in an inert organic solvent by the known methods to yield the corresponding di- and polyisocyanates of the diphenylmethane series, MDI. The molar ratio of crude MDA to phosgene is expediently chosen such that 1 to 10 mol, and preferably 1.3 to 4 mol, of phosgene are present in the reaction mixture per mol of $NH_2$ group. Chlorinated aromatic hydrocarbons such as, for example, monochlorobenzene, dichlorobenzenes, trichlorobenzenes, the corresponding toluenes and xylenes and chloroethylbenzene, have proved to be suitable inert solvents. Monochlorobenzene, dichlorobenzene or mixtures of these chlorobenzenes are preferably used as inert organic solvents. The amount of solvent is expediently chosen such that the reaction mixture has an isocyanate content of 2 to 50 wt %, preferably between 5 and 25 wt %, based on the total weight of the reaction mixture. When the phosgenation has ended, the excess phosgene, the inert organic solvent and/or mixtures thereof, are separated off from the reaction mixture by distillation.

The products of the polymeric MDI series containing di- and polyisocyanates of the diphenylmethane series which are dinuclear and more than dinuclear, and of the monomeric MDI series containing dinuclear diisocyanates of the diphenylmethane series, can be prepared from the crude MDI obtained. In particular, high-viscosity polymeric MDI types of 80 to 3000 mPas at 25° C., technical-grade 4,4'-MDI and/or technical-grade 2,4'-MDI as well as mixed forms thereof can be prepared. These products can be separated off from the crude MDI in accordance with the prior art, for example, by distillation. These products are suitable for use as raw materials for polyurethane preparation in the form of polymers and prepolymers by reaction with polyols.

Products made according to the present invention using formalin with the claimed low levels of divalent or more than divalent metals show controlled reactivity with these polyols this contrary to products made using formalin containing higher levels of these metals.

The following examples further illustrate details for the process of this invention. The invention, which is set forth in the foregoing disclosure, is not to be limited either in spirit or scope by these examples. Those skilled in the art will readily understand that known variations of the conditions of, the following procedures can be used. Unless otherwise noted, all temperatures are degrees Celsius and all percentages are percentages by weight.

EXAMPLES

Aniline (111,756 g) (1.2 mol) was placed in a glass 3-neck flask, under stirring with a reflux condenser. To the aniline solution, 11.82 g of 37 wt % strength aqueous hydrochloric acid (0.12 mol) was added at 30° C. under stirring. The mixture was then stirred at 50° C. for 20 minutes. Formaldehyde was used as an aqueous solution, commonly termed formalin. Two grades of formaldehyde solution were used:

1) High stability grade (Sigma-Aldrich): 40.58 g of a 37 wt % strength aqueous formaldehyde solution (0.5 mol) which contains about 10 wt % methanol to limit the extent of polymerization during storage 2) Low stability grade: 31.95 g of a 47 wt % strength aqueous formaldehyde solution (0.5 mol) which contains about 1 wt % methanol to limit the extent of polymerization and a stabilizer.

The formaldehyde solution was added drop-wise to the aniline/HCl mixture over a period of 30 minutes using a dropping funnel and the temperature was kept below 80° C. For the purposes of demonstration, metal ions were added to the high purity formalin in the form of chloride salts. The quantity of metal ions present in each formaldehyde solution is indicated in Table 1.

After the addition was completed, the mixture was stirred for a further 4 hours at 100° C., under reflux, and was put in an oven at 90° C. overnight.

The following day, the mixture was neutralized with 17.45 g of a 33 wt % sodium hydroxide solution.

The results are indicated in the table below.

From the table, it can be seen that no solids and no rag layer is formed when the total metal ion content in the formaldehyde solution is less than $3 \times 10^{-4}$ wt %. At slightly higher levels, a small amount of solid material can be observed but this is insufficient to form a real rag layer and in practice such an amount would not constitute a serious problem for operation of a large scale production plant which could thus continue operating for an extended period of time.

TABLE 1

| Exp | Formalin Stabilisation | Al (wt. %) | Ca (wt. %) | Fe (wt. %) | Mg (wt. %) | Total (wt. %) | Solids/Rag layer? |
|---|---|---|---|---|---|---|---|
| 1 | High | 0 | 0 | 0 | 0 | $<3*10^{-4}$ | no |
| 2 | High | 0 | $6.0*10^{-5}$ | 0 | $2.2*10^{-5}$ | $<3*10^{-4}$ | no |
| 3 | High | 0 | $1.2*10^{-4}$ | 0 | $4.4*10^{-5}$ | $<3*10^{-4}$ | no |
| 4 | Low | 0 | $1.5*10^{-4}$ | 0 | $5.6*10^{-5}$ | $<3*10^{-4}$ | no |
| 5 | High | 0 | $2.4*10^{-4}$ | 0 | 0 | $<3*10^{-4}$ | no |
| 6 | High | 0 | $2.4*10^{-4}$ | 0 | $8.8*10^{-5}$ | $<5*10^{-4}$ | solids - no rag layer |
| 7 | Low | 0 | $3.0*10^{-4}$ | 0 | $1.1*10^{-4}$ | $<5*10^{-4}$ | solids - no rag layer |
| 8 | High | 0 | $3.7*10^{-4}$ | 0 | 0 | $<5*10^{-4}$ | solids - no rag layer |
| 9 | High | $3.4*10^{-4}$ | $3.7*10^{-4}$ | $6.7*10^{-4}$ | $1.3*10^{-4}$ | $>1*10^{-3}$ | yes |
| 10 | High | 0 | $3.7*10^{-3}$ | 0 | $1.3*10^{-3}$ | $>1*10^{-3}$ | yes |
| 11 | High | $6.7*10^{-3}$ | $7.4*10^{-3}$ | $1.3*10^{-2}$ | $2.7*10^{-3}$ | $>1*10^{-3}$ | yes |

The invention claimed is:

1. A process for the preparation of di- and polyamines of the diphenylmethane series comprising reacting aniline with formaldehyde in the presence of hydrochloric acid, characterised in that the formaldehyde employed is used as an aqueous solution which contains less than 0.001 wt % of metal ions which are divalent and/or more than divalent wherein the formaldehyde employed is used as an aqueous solution which contains metal ions selected from the group consisting of Ca2+, Mg2+, Al3+ and Fe2+.

2. Process according to claim 1, wherein the formaldehyde employed is used as an aqueous solution which contains less than 0.0005 wt % of metal ions which are divalent and/or more than divalent.

3. Process according to claim 2, wherein the formaldehyde employed is used as an aqueous solution which contains less than 0.0003 wt % of metal ions which are divalent and/or more than divalent.

4. Process according to claim 1, wherein the concentration of individual metal ions which are divalent and/or more than divalent is less than 0.0003 wt %.

5. Process according to claim 1, wherein the hydrochloric acid contains less than 0.001 wt % of metal ions which are divalent and/or more than divalent.

6. Process according to claim 1, wherein the reaction of aniline with formaldehyde in the presence of hydrochloric acid is carried out with a degree of protonation of less than 20%.

7. Process according to claim 1, wherein the reaction mixture is subsequently neutralised with a base.

8. Process according to claim 7, wherein the organic phase is subsequently separated from the aqueous phase.

9. Process according to claim 1 wherein the di- and polyamines of the diphenylmethane series are subsequently converted into the corresponding di- and polyisocyanates of the diphenylmethane series by reacting with phosgene.

10. Process according to claim 1, wherein on-line analysis based on methods employing the characteristic electronic transitions which occur within the metal ions or mass spectrometric techniques is used for process monitoring or process control of the purity of the used aqueous formaldehyde solution.

11. A process for the preparation of di- and polyamines of the diphenylmethane series comprising reacting aniline with formaldehyde in the presence of hydrochloric acid, characterised in that the formaldehyde employed is used as an aqueous solution which contains less than 0.001 wt % of metal ions which are divalent and/or more than divalent and wherein the hydrochloric acid contains less than 0.001 wt % of metal ions which are divalent and/or more than divalent.

* * * * *